(12) United States Patent
Riesgo et al.

(10) Patent No.: US 7,838,481 B2
(45) Date of Patent: Nov. 23, 2010

(54) FORMALDEHYDE-FREE CLEANER COMPOSITION FOR CLEANING BLOOD ANALYZERS AND METHOD OF USE

(75) Inventors: Mirta I. Riesgo, Miami, FL (US); Carlos S. Rubio, Hialeah, FL (US); Susana M. Maldonado, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 1083 days.

(21) Appl. No.: 11/399,813

(22) Filed: Apr. 7, 2006

(65) Prior Publication Data

US 2007/0238632 A1    Oct. 11, 2007

(51) Int. Cl.
*C11D 3/20* (2006.01)

(52) U.S. Cl. .................. 510/161; 510/179; 510/382; 510/386

(58) Field of Classification Search ............ None
See application file for complete search history.

(56) References Cited

U.S. PATENT DOCUMENTS

| | | | |
|---|---|---|---|
| 5,234,832 A | 8/1993 | Disch et al. | |
| 5,587,356 A * | 12/1996 | Dauderman et al. | 510/320 |
| 5,589,448 A | 12/1996 | Koerner et al. | |
| 5,783,537 A | 7/1998 | Ahmed et al. | |
| 5,858,117 A | 1/1999 | Oakes et al. | |
| 5,877,141 A | 3/1999 | Gabriel et al. | |
| 5,975,095 A | 11/1999 | Ahmed et al. | |
| 6,017,871 A | 1/2000 | Baeck et al. | |
| 6,020,293 A | 2/2000 | Ahmed et al. | |
| 6,165,966 A | 12/2000 | McIver et al. | |
| 6,251,845 B1 | 6/2001 | Herbots et al. | |
| 2002/0082188 A1 * | 6/2002 | Baker et al. | 510/475 |
| 2003/0039580 A1 * | 2/2003 | Borokhov et al. | 422/37 |
| 2003/0166290 A1 | 9/2003 | Lang et al. | |

FOREIGN PATENT DOCUMENTS

EP    0743356 B1    10/2002

\* cited by examiner

*Primary Examiner*—Duy-Vu N Deo
(74) *Attorney, Agent, or Firm*—Cuspa Technology Law Associates; Mitchell E. Alter

(57) ABSTRACT

A formaldehyde-free cleaner composition and method of use for maintaining a blood analyzer are disclosed. The cleaner composition includes surfactants, a proteolytic enzyme, non-formaldehyde releasing antimicrobials, alkaline metal salts, and a buffer. The cleaner composition has a pH in a range from about 7 to about 12 and a formaldehyde concentration equal or less than 1 ppm.

24 Claims, No Drawings

FORMALDEHYDE-FREE CLEANER COMPOSITION FOR CLEANING BLOOD ANALYZERS AND METHOD OF USE

FIELD OF THE INVENTION

The present invention relates to a cleaner composition and method of use for cleaning automated blood analyzers, more particularly relates to a cleaner composition that is substantially free of formaldehyde content.

BACKGROUND OF THE INVENTION

An effective cleaning reagent and cleaning procedures are necessary for automated and semi-automated blood analyzers for cleaning the instrument components that are in contact with the blood samples, or the mixtures of a blood sample and the reagents used for blood analysis, and maintaining the analyzers in proper operating conditions. During blood sample analysis, for example on automated hematology analyzers, the whole blood sample will be treated with various reagents on the instrument prior to the measurement. Typically, an aliquot of a whole blood sample is diluted by an isotonic diluent to form a sample mixture for the red blood cell and platelet measurements. Another aliquot of the whole blood sample is mixed with a lytic reagent to form a second sample mixture for the white blood cell and hemoglobin measurements, wherein the red blood cells are lysed. These sample mixtures of the blood sample and the reagents contain proteins, and debris from the lysed cellular membranes. These materials can precipitate on the surface of certain instrument components which are in contact with the sample mixtures during the analysis of the blood sample. Furthermore, these materials can also form insoluble complexes with certain chemicals in the reagent and precipitate on the surface of the instrument components. Without an effective cleaning on a regular basis, the precipitates can build up around the apertures and flow cell, which are used for blood cell counting, and along the wall of tubings that are in contact with the sample mixtures. This can cause partial or complete clogging of the apertures or flow cell, rendering the instrument inoperable.

Enzymatic cleaning reagents are known in the art, and they are effective in breaking down the proteins and blood debris by enzymatic reactions. Surfactants are commonly used in the cleaning reagents for dissolving or dispersing the debris and large organic molecules.

Antimicrobials are commonly used in the cleaning reagents as preservatives to inhibit the growth of microorganisms, such as bacteria, fungi, and yeast, and to ensure shelf-life, quality and performance of the reagent products. Furthermore, it is also important to prevent microorganism growth inside the instruments, such as inside the reagent tubings and other parts of the fluid feeding system, because organism growth can cause contamination of the instrument components, and can further interfere with system performance. For example, the organisms can be counted as blood cells, or cause false flaggings which indicate the presence of abnormal blood types in a blood sample.

The majority of commonly used antimicrobials are formaldehyde-releasing agents, which contain or release formaldehyde during storage. These formaldehyde-releasing agents are strong antimicrobials and are very effective in inhibiting the growth of organisms in aqueous solutions. However, the formaldehyde contained in a cleaning reagent released through the instrument effluent has caused environmental concerns in recent years.

In the past decade, the regulations for institutional, industrial and medical waste content increase as certain chemicals are found to pose a threat to human health and/or to the environment. Regulation agencies in several states, such as California and Massachusetts, have implemented new regulations on waste content allowance. Formaldehyde is one of the chemicals that are restricted in the waste in these two states. According to the new regulation, formaldehyde concentration in the waste equal or less than 1 ppm is considered formaldehyde-free.

Therefore, there is a strong need for a formaldehyde-free cleaning reagent that is effective cleaning the blood analyzers, stable during storage, and environmentally friendly.

SUMMARY OF THE INVENTION

In one embodiment, the present invention is directed to a formaldehyde-free cleaner composition, which comprises one or more surfactant and one or more non-formaldehyde releasing antimicrobial in an aqueous solution. The cleaner composition further comprises a proteolytic enzyme, an alkaline metal salt, and a buffer to maintain the pH of the cleaner composition in a range from about 7 to about 12, preferably from about 8 to about 10. The cleaner composition has a formaldehyde concentration equal or less than 1 ppm.

Preferably, an isothiazolone compound is used as the antimicrobial, more preferably, two or more isothiazolone compounds are used in the cleaner composition to preserve the composition and to support maintaining the blood analyzer. Preferably, the surfactant is a nonionic surfactant, an anionic surfactant, or their combinations, and the proteolytic enzyme is a subtilisin.

In a further embodiment, the present invention is directed to a method of cleaning a blood analyzer, which comprises the steps of providing a formaldehyde-free cleaner composition to a blood analyzer; delivering the cleaner composition to the parts of the blood analyzer, which are in contact with a sample mixture formed by a blood sample and one or more reagent during an analysis of the blood sample; contacting the parts with the cleaner composition for a period of time; and rinsing the cleaner composition out from the blood analyzer. The blood analyzers include hematology analyzers, flow cytometers, or clinical chemistry analyzers.

The advantages of the present invention will become apparent from the hereinafter set forth Detailed Description of the Invention, and Claims appended herewith.

DETAILED DESCRIPTION OF THE INVENTION

In one embodiment, the present invention provides a formaldehyde-free aqueous cleaner composition, which comprises one or more surfactant and one or more non-formaldehyde releasing antimicrobial. Preferably, the cleaner composition further comprises a proteolytic enzyme; one or more alkaline metal salt; and a buffer to maintain a pH of the cleaner composition in a range from about 7 to about 12. The cleaner composition is substantially free of formaldehyde. In a preferred embodiment, the cleaner composition has a formaldehyde concentration equal or less than 1 part per million (ppm).

The term "substantially free of formaldehyde" used herein means that the formaldehyde concentration of an aqueous composition meets the formaldehyde-free definition of the Environmental Protection Agency (EPA), which specifies that as assayed by a defined HPLC analysis method (EPA Method 8315A), the formaldehyde concentration of an aqueous composition is equal or less than 1 ppm.

Surfactants suitable for the cleaner composition of the present invention include nonionic surfactant, anionic surfactant, or combinations thereof. Suitable examples of nonionic surfactant include, but are not limited to, ethoxylated alkyl phenol, ethoxylated alkyl alcohol, or combinations thereof. Preferably, the ethoxylated alkyl alcohol has a linear alkyl group having 8 to 18 carbon atoms and 10 to 40 moles of ethylene oxide; and the ethoxylated alkyl phenol can have either a linear alkyl group or branched alkyl groups having 6 to 10 carbon atoms and 4 to 30 moles of ethylene oxide. In an exemplary embodiment, a combination of two ethoxylated nonyl phenols is used. Suitable examples of anionic surfactant include, but are not limited to, ethoxylated alkyl phenol phosphate ester, ethoxylated alkyl phosphate ester, and ethoxylated alkyl sulfate ester. Preferably, the ethoxylated alkyl phenol phosphate ester has a linear alkyl group having 8 to 10 carbon atoms, and 4 to 30 moles of ethylene oxide. In another exemplary embodiment, a combination of an ethoxylated nonyl phenol and an ethoxylated alkyl phenol phosphate ester is used. The concentration of the surfactant(s) in the cleaner composition can be in a range from about 1 g/l to about 30 g/l.

Proteolytic enzyme or protease is any enzyme that catalyzes the splitting of proteins into smaller peptide fractions and amino acids by a process known as proteolysis. Proteolytic enzymes of various qualities and origins and having activity in various pH ranges of from 7-12 are available and can be used in the present invention. Examples of suitable proteolytic enzymes are the subtilisins which are obtained from particular strains of $B.\ subtilis,\ B.\ licheniformis$, such as the commercially available subtilisins Maxatase™, as supplied by Genencor International N. V., Delft, Holland, and Alcalase™ as supplied by Novozymes Industri A/S, Copenhagen, Denmark.

Particularly suitable is a protease obtained from a strain of $Bacillus$ having maximum activity throughout the pH range of 8-12, being commercially available from Novozymes Industri A/S under the tradenames Esperase® and Savinase®. The preparation of these and analogous enzymes is described in GB 1 243 785. Other commercial available proteases are Kazusase™ (from Showa-Denko of Japan), Optimase™ (from Miles Kali-Chemie, Hannover, West Germany), and Superase™ (from Pfizer of the United States).

The concentration of the proteolytic enzyme in the cleaner composition can be in a range from about 0.15 μg/ml to about 500 μg/ml. It is noted that the concentration described herein is expressed by the amount of pure enzyme in the cleaner composition.

It is well known that enzymes may become denatured in storage. A number of enzyme stabilizing systems have been developed and are well known in the enzyme formulation art. It has been found that one or more alkaline metal salts are effective in stabilizing the proteolytic enzyme in the cleaner composition of the present invention. Preferably, alkaline metal formate, or alkaline metal halide can be used. More preferably, a combination of alkaline metal formate and alkaline metal halide is used. In an exemplary embodiment shown in Example 1, sodium formate and sodium chloride are used. The concentration of the alkaline metal salt or salts in the cleaner composition can be in a range from about 1 g/l to about 16 g/l.

Various inorganic or organic buffers can be used for maintaining pH of the cleaner composition. Suitable buffers include, but are not limited to, sodium carbonate, sodium bicarbonate, boric acid, glycylglycine, glycine, tris hydroxymethylaminoethane (TRIS), N-tris(hydroxymethyl) methyl-2-aminoethane sulfonic acid (TES), N-2-hydroxyethylpiperazine-N'-2-ethanesulfonic acid (HEPES), N-2-hydroxyethylpiperazine-N'-3-propane sulfonic acid (HEPPS), 2-(N-cyclohexylamino) ethane sulfonic acid (CHES), piperazine-1,4-bis(2-ethane sulfonic acid) (PIPES), 3-((tris(hydroxymethyl)methyl)amino)propanesulfonic acid (TAPS), or combinations thereof. In one exemplary embodiment, tris hydroxymethylaminoethane is used. pH of the cleaner composition of the present invention is in the range from about 7 to about 12, preferably, from about 8 to about 10.

Proper selection of antimicrobials used in the cleaner composition can ensure shelf-life of the reagent, and also reduce potential organism growth inside the blood analyzers. As described previously, the majority of commonly used antimicrobials are formaldehyde-releasing agents. Because of the potential environmental contamination from formaldehyde contained in the instrument effluent, formaldehyde-releasing agents are not the choice antimicrobials in the cleaner composition of the present invention. Only non-formaldehyde releasing antimicrobials are used as the preservative of the aqueous reagent and as the active component for inhibiting microbial growth in the blood analyzers. The term "formaldehyde-releasing agent" used herein refers to any chemical which contains or releases, upon chemical reaction, formaldehyde molecule. The term "non-formaldehyde releasing antimicrobial" used herein refers to a chemical which has antimicrobial function, but does not contain, or release formaldehyde during storage of a reagent product which contains the antimicrobial.

Various commercially available non-formaldehyde releasing antimicrobials can be used for the purpose of the present invention. These include, but are not limited to, isothiazolone compounds, phenoxyethanol, 2(2-phenoxyethoxy) methyldibromoglutaronitrile, amine abduct, 2,2-dibromo-3-nitriloprionamide, or combinations thereof. Particularly suitable are isothiazolone compounds. Suitable examples of isothiazolone compounds include 5-chloro-2-methyl-4-isothiazolin-3-one, 2-methyl-4-isothiazolin-3-one, 1,2 benzisothiazolin-3-one, and derivatives thereof. Herein the term "derivatives" refers to homologs which are the compounds differing regularly by the successive addition of the same chemical group, e.g., by —$CH_2$— groups, or differing by changing one with another among halide functional group. Commercially, Proclin® 150, which contains a mixture of 5-chloro-2-methyl-4-isothiazolin-3-one and 2-methyl-4-isothiazolin-3-one, can be obtained from Rohm and Haas Company, Philadelphia, Pa. 1,2 benzisothiazolin-3-one is commercially available under the tradenames Mergal® K10N from Troy Corporation, Florham Park, N.J., and Acticide® B10 from Thor gmbh Speyer, Germany.

Preferably, two or more non-formaldehyde releasing antimicrobials are used together to achieve a synergetic effect in inhibiting the growth of a broad spectrum of organisms including bacteria, fungi, and yeast, particularly those frequently observed in the automated blood analyzer systems. In one exemplary embodiment, a combination of 5-chloro-2-methyl-4-isothiazolin-3-one, 2-methyl-4-isothiazolin-3-one, and 1, 2 benzisothiazolin-3-one is used in the cleaner composition, as shown in Example 1 hereinafter. The concentration of the antimicrobial(s) in the cleaner composition can be in a range from about 0.03 g/l to about 0.8 g/l.

To ensure the antimicrobial effectiveness in the reagent product, typically preservative effectiveness test, also referred to as microbiological challenge study, is performed using the standard procedures known in the art. According to United States Pharmacopeia (USP) 26, Chapter 51, the formulation is effective when the following are true:

Bacteria: Not less than 1.0 $\text{Log}_{10}$ reduction from the initial calculated count at 7 days, not less than 3.0 $\text{Log}_{10}$ reduction from the initial count at 14 days, and no increase from the 14 day's count at 28 days.

Yeast and molds: No increase from the initial calculated count at 7, 14, and 28 days.

Example 2 illustrates preservative effectiveness tests of two cleaner compositions, Formula A and Formula B of Example 1. As shown in Table 2, the inoculation levels of all organisms tested were reduced from $10^5$ to below $10^2$ (CFU/ml) in Formula A as early as 48 hours, and the inoculation levels were maintained below $10^2$ (CFU/ml) during the tests at 7, 14 and 28 days. As further shown in Table 3, the antimicrobials in Formula B were effective in eliminating all organisms tested in a 48 hour period of time, which was substantially shorter than 7 days as required by USP 26.

The concentration of formaldehyde is analyzed using high performance liquid chromatography (HPLC) according to EPA Method 8315A. The cleaner composition is sampled into clean containers, immediately after it is manufactured, or after it is stored at room temperature or at elevated temperatures. The samples are sent to a certified analytic laboratory for analysis of the formaldehyde content. It is known that in some aqueous compositions stored under elevated temperatures, or stored at room temperature for a substantial period of time, the formaldehyde concentration may increase from the level when it is freshly made. Various storage conditions that may occur during product shipping and customer uses, for example storing at room temperature and at elevated temperatures up to 40° C., have been tested. Under all conditions, the analyses have shown that the cleaner composition of the present invention is substantially free of formaldehyde. As further described in detail in Example 3, the formaldehyde concentration of the cleaner composition is less than 1 ppm when it is freshly made, and remains less than 1 ppm Under various storage conditions.

In a further aspect, the present invention provides a method of cleaning, or maintaining a blood analyzer using the formaldehyde-free cleaner composition of the present invention. The term "blood analyzer" used herein refers to automated or semi-automated instruments used for analyzing blood samples, such as hematology analyzers, flow cytometers, and clinical chemistry analyzers. In one embodiment, the cleaner composition is automatically delivered by an automated blood analyzer to the components or parts of the instrument, which contact the sample mixture formed by a blood sample and one or more reagent, during blood analysis, the cleaner composition is kept in contact with these instrument components for a period of time, and rinsed out with a diluent or water. Optionally, air-mixing the cleaner composition by air flow or bubbling can also be utilized to increase physical agitation on the surfaces of the components. During the above-described cleaning process, the cleaner composition removes precipitates built up on the surfaces of the components, which are generated from debris, or protein precipitates from lysed blood samples, or chemical complexes formed between blood components and the reagents used for blood analysis; therefore, it maintains the instrument components clean and prevents undesired build-ups on the surfaces of these components. The cleaning process can be carried out one or more times daily, depending on the usage or workload of the instrument.

On a hematology analyzer, the cleaner composition is usually delivered to the instrument components, such as chambers for preparing the blood sample, flow cells, apertures and tubings which are in contact with the sample mixture during analysis, after regular use of the instrument, typically at the instrument shutdown time. The contact time, or incubation time, of the cleaner composition with the instrument components can be programmed on the automated instrument, typically from 10 minutes to 12 hours, and can be even longer. With various existing hematology analyzers, typically at the shutdown time the instrument is rinsed one or more times with the cleaner composition, and the cleaner composition is delivered again and maintained in the chambers and the tubings overnight, then rinsed out from the system at the start up time in the next day. The cleaning process is also commonly performed once at the end of each shift in clinical hematology laboratories, when the instruments are used for all three shifts a day. Alternatively, an automated cleaning cycle can also be programmed into the instrument system, which automatically carries out the cleaning process after a predetermined number of samples have been analyzed on the instrument. The cleaner composition is typically rinsed out using a blood diluent which is used for blood analysis in the blood analyzer. However, it can also be rinsed out by water.

The frequency of the cleaning process and the contact time of the cleaner composition with the instrument components can be determined by the instrument manufacturer based on the instrument's needs, and it can also be determined by the laboratories based on the workload of the instrument.

It has been found that using the cleaner composition and the method of the present invention a blood analyzer, particularly those high end hematology analyzers which typically analyze several hundreds of whole blood samples daily, can be effectively cleaned, and maintained no precipitates built up after a substantial amount of blood samples have been analyzed on the instruments. Example 4 illustrates an example using a cleaner composition of the present invention for maintaining a Coulter LH750 hematology analyzer (product of Beckman Coulter, Inc., Fullerton, Calif.). As shown, after running about 1,100 blood analysis cycles under a stressed instrument working environment in a period of two weeks, no precipitation on the surface around the apertures was observed. It is known that because of the electrical voltage applied around the apertures these areas often show precipitate built up when a large number of blood samples are analyzed. Therefore, the efficiency of a cleaner composition in cleaning and maintaining a blood analyzer can be tested effectively by monitoring the surfaces of these areas during the test.

The following examples are illustrative of the invention and are in no way to be interpreted as limiting the scope of the invention, as defined in the claims.

EXAMPLE 1

The following enzymatic cleaner compositions were prepared.

| Formula A | |
|---|---|
| TRIS | 6.05 g |
| 1,2 benzisothiazolin-3-one* | 0.098 g |
| 5-chloro-2-methyl-4-isothiazolin-3-one | 17.0 mg |
| 2-methyl-4-isothiazolin-3-one | 5.70 mg |
| Sodium formate | 8.16 g |
| Sodium chloride | 3.5 g |
| Ethoxylated nonylphenol | 1.98 g |
| Ethoxylated branched nonylphenol | 1.40 g |
| Proteolytic enzyme | $4.96 \times 10^{-3}$ μg |
| Patent Blue VF | 0.015 g |
| q.a. to 1.0 liter by deionized water | |
| pH | 8.70 |
| Formaldehyde concentration: | 0.4 ppm |

| Formula B | |
|---|---|
| TRIS | 6.05 g |
| 1,2 benzisothiazolin-3-one** | 0.10 g |
| 5-chloro-2-methyl-4-isothiazolin-3-one | 17.0 mg |
| 2-methyl-4-isothiazolin-3-one | 5.70 mg |
| Sodium formate | 8.16 g |
| Sodium chloride | 3.5 g |
| Ethoxylated nonylphenol | 1.98 g |
| Ethoxylated branched nonylphenol | 0.70 g |
| Ethoxylated alkyl phosphate ester | 8.5 g |
| Proteolytic enzyme | $4.96 \times 10^{-3}$ μg |
| Patent Blue VF | 0.015 g |
| q.a. to 1.0 liter by deionized water | |
| pH | 8.70 |
| Formaldehyde concentration: | 0.6 ppm |

5-chloro-2-methyl-4-isothiazolin-3-one and 2-methyl-4-isothiazolin-3-one were obtained from Rohm and Hass, Philadelphia, Pa., under the tradename Proclin® 150. 1,2 benzisothiazolin-3-one was obtained from Troy Corporation, Florham Park, N.J., under the tradename Mergal® K10N(*) and from Thor gmbh Speyer, Germany, under the tradename Acticide® B10(**), respectively. Ethoxylated alkyl phosphate ester was obtained from Murnco, Bloomington, Minn. Ethoxylated nonyl phenol was obtained from Sigma/Aldrich, St. Louis, Mo., under the tradename Nonidet® P-40 Substitute. Ethoxylated branched nonyl phenol was obtained from Rhone-Poulenc, Cranbury, N.J., under the tradename Igepal SS-837. Protease was obtained from Novo Nordisk Biochem North America, Inc., Fraanklinton, N.C., under the tradename Esperase® 8.0L.

EXAMPLE 2

Preservative Effectiveness Test was performed on Formula A of Example 1 to determine antimicrobial effectiveness of the cleaner composition.

The Preservative Effectiveness Test is a measure of the ability of an antimicrobial to limit the proliferation of bacterial, yeast and mold cells and/or spores at or below the levels and conditions stated in the USP 26 (United States Pharmacopeia 26, Chapter 51) Preservative Effectiveness Test.

The cleaner composition was first tested for initial sterility by inoculating 0.5 ml of the cleaner composition into nutrient broth tubes and incubating for seven days at 20-25° C. and 30-35° C. No organism was observed in the incubated samples.

The cleaner composition was tested against eleven organisms including six bacteria, two yeasts, and three fungi. Five of the organisms were listed in USP 26, and six organisms were previously isolated from hematology analyzers having contamination from organism growth. The organisms were prepared according to microbiology standard procedures to obtain initial suspensions containing approximately $1 \times 10^7$ to $1 \times 10^8$ CFU (colony forming units)/ml. 10 ml of a cleaner composition in a sample tube was inoculated with 50 μl of the initial suspension for each of the organisms to obtain a concentration of each organism in the cleaner composition between $1 \times 10^5$ and $1 \times 10^6$ CFU/ml. The inoculation levels used in the preservative effectiveness test were shown in Table 1.

The inoculated sample tubes were mixed and incubated according to USP 26. The inoculated cleaner compositions were diluted in the saline blank, and plated out using standard plate count methodology. The plates were incubated according to the microbial recovery incubation times in USP 26. Following incubation, colony forming units were enumerated and reported.

TABLE 1

Inoculation Levels

| ORGANISM | ATCC NO. | INOCULUM LEVEL CFU/ml |
|---|---|---|
| E. coli | 8739 | $6.7 \times 10^5$ |
| S. aureus | 6538 | $6.0 \times 10^5$ |
| P. aeruginosa | 9027 | $5.7 \times 10^5$ |
| P. cepacia | Isolate* | $5.8 \times 10^5$ |
| Corynebacterium sp. | Isolate* | $8.5 \times 10^5$ |
| Bacillus sp. | Isolate* | $1.5 \times 10^5$ |
| C. albicans | 10231 | $6.5 \times 10^5$ |
| C. lipolytica | Isolate* | $4.7 \times 10^5$ |
| A. niger | 16404 | $5.9 \times 10^5$ |
| Paecilomyces sp. | Isolate* | $3.1 \times 10^5$ |
| Penicillium sp. | Isolate* | $8.9 \times 10^5$ |

*the organism was isolated from hematology analyzers having contamination from organism growth.

The inoculated cleaner composition was evaluated at 48 hours, 7, 14, 21 and 28 days. The results at 48 hours, 7, 14 and 28 days are shown in Table 2. As shown, no growth of all organisms tested was observed in Formula A. It was noted that the inoculation levels were reduced to less than $10^2$ (CFU/ml) as early as 48 hours, and were maintained below $10^2$ (CFU/ml) during the 28 day test period. The results showed that the antimicrobials in Formula A were effective in preserving the cleaner composition.

TABLE 2

Preservative Effectiveness Test Results

| ORGANISM | 48 hours CFU/ml | 7 days CFU/ml | 14 days CFU/ml | 28 days CFU/ml |
|---|---|---|---|---|
| E. coli | <100 | <100 | <100 | <100 |
| S. aureus | <100 | <100 | <100 | <100 |
| P. aeruginosa | <100 | <100 | <100 | <100 |
| P. cepacia | <100 | <100 | <100 | <100 |
| Corynebacterium sp. | <100 | <100 | <100 | <100 |
| Bacillus sp. | <100 | <100 | <100 | <100 |
| C. albicans | <100 | <100 | <100 | <100 |
| C. lipolytica | <100 | <100 | <100 | <100 |
| A. niger | <100 | <100 | <100 | <100 |
| Paecilomyces sp. | <100 | <100 | <100 | <100 |
| Penicillium sp. | <100 | <100 | <100 | <100 |
| Negative Control | No Growth | No Growth | No Growth | No Growth |

Formula B of Example 1 was tested using the same panel of organisms shown in Table 1 at equivalent inoculation levels using the same procedure described above. The inoculated cleaner composition was evaluated at 48 hours and the results are shown in Table 3.

As shown, no growth of all organisms tested was observed in Formula B. The antimicrobials in Formula B were effective in eliminating all organisms tested in a 48 hour period of time, which was substantially shorter than 7 days as required by USP 26.

TABLE 3

Preservative Effectiveness Test Results

| ORGANISM | 48 hours CFU/ml |
|---|---|
| E. coli | <100 |
| S. aureus | <100 |
| P. aeruginosa | <100 |
| P. cepacia | <100 |
| Corynebacterium sp. | <100 |
| Bacillus sp. | <100 |
| C. albicans | <100 |
| C. lipolytica | <100 |
| A. niger | <100 |
| Paecilomyces sp. | <100 |
| Penicillium sp. | <100 |
| Negative Control | No Growth |

EXAMPLE 3

Formula A of Example 1 was sampled at various times, including right after the cleaner composition was made, referred to as fresh, and after incubating the cleaner composition at 45° C. for 17 and 35 days. Incubation at the elevated temperature provided an accelerated reagent stability test condition. The samples were sent to Adirondack Environmental Services, Inc., Albany, N.Y., for analysis. Adirondack Environmental Services, Inc. is certified by National Environmental Laboratory Approval Program. Formaldehyde concentration of the cleaner composition was analyzed using HLPC according to the procedure described in EPA Method 8315A. The analysis results are shown in Table 4.

TABLE 4

Formaldehyde Concentrations in the Cleaner Compositions

| | Formaldehyde Concentration (ppm) | | |
|---|---|---|---|
| Lot Number | Fresh | 17 days | 35 days |
| Lot No. 1 | 0.408 | 0.502 | 0.796 |
| Lot No. 2 | 0.150 | 0.234 | 0.287 |
| Lot No. 3 | 0.115 | 0.429 | 0.217 |

As shown, either at the time that the cleaner composition was produced, or after it was stored under an accelerated stability test condition, the formaldehyde concentration maintained less than 1 ppm.

EXAMPLE 4

A Coulter LH750 hematology analyzer (product of Beckman Coulter, Inc., Fullerton, Calif.) was used in a performance test of the cleaner composition of the present invention. The Coulter Clenz®, an existing cleaner product of Beckman Coulter, Inc., connected to instrument was replaced by Formula A of Example 1. An eleven working day stress test was performed on the hematology analyzer, which simulated a stressed instrument working environment. During the eleven day test period, there were two weekends. Each day, after the instrument's regular start up cycle, a quality control procedure was performed, as recommended to the instrument users, which involved testing various blood control products. Then, seven fresh whole blood samples and seven 24-hour old whole blood samples were run on the instrument according to the standard procedure described in the Operator Manual, and each sample was analyzed six times. Moreover, expired blood controls were analyzed eighteen times on the instrument. The expired blood control was generally more viscous, and was known to have a tendency causing cleaning difficulties. For each of the eleven days, a shutdown cycle was run at the end of the day. For five days, a 30 minute shutdown cycle was run; for another five days, a 12 hour shutdown cycle was run; and for one day a 24 hour shutdown cycle was run. During the shutdown cycle, the cleaner composition was delivered in various areas of the instrument, being in contact with apertures, sample mixing chambers, and various tubings. After each shutdown cycle, a start up cycle was run, and the cleaner composition was rinsed out from the instrument by LH700 Series Diluent (product of Beckman Coulter, Inc.).

After the eleven day stress test as described above, the apertures in the WBC bath and RBC bath were removed from the instrument, and examined visually and under a stereoscope. No precipitate buildup from proteins and debris was observed on the surfaces of apertures and surrounding areas. Furthermore, no precipitate was observed in the tubings and other components which were in contact with the blood sample/reagent mixtures during the analysis of the blood samples.

While the present invention has been described in detail, this should not be construed as a limitation on the scope of the present invention, but rather as an exemplification of preferred embodiments thereof. It will be apparent, however, that various modifications and changes can be made within the spirit and the scope of this invention as described in the above specification and defined in the appended claims and their legal equivalents.

What is claimed is:

1. A formaldehyde-free cleaner composition comprising an aqueous solution of:
   (a) one or more surfactant;
   (b) a combination of two or more isothiazolone compounds, said isothiazolone compounds being in a concentration range from about 0.03 g/l to about 0.8 g/l;
   (c) a proteolytic enzyme;
   (d) one or more alkaline metal salt; and
   (e) a buffer to maintain a pH of said cleaner composition in a range from about 7 to about 12;
   said cleaner composition being absent of formaldehyde-releasing agent and having a formaldehyde concentration equal or less than 1 ppm, and being effective in inhibiting growths of bacteria, yeasts and fungi in a blood analyzer.

2. The cleaner composition of claim 1, wherein said isothiazolone compounds comprise 5-chloro-2-methyl-4-isothiazolin-3-one, 2-methyl-4-isothiazolin-3-one, 1, 2 benzisothiazolin-3-one, or derivatives thereof.

3. The cleaner composition of claim 1, wherein said surfactant is a nonionic surfactant, an anionic surfactant, or combinations thereof.

4. The cleaner composition of claim 1, wherein said proteolytic enzyme is a subtilisin.

5. The cleaner composition of claim 4 wherein said subtilisin is in a concentration range from about 0.15 µg/ml to about 500 µg/ml.

6. The cleaner composition of claim 1, wherein said alkaline metal salt is an alkaline metal halide, an alkaline metal formate, or combinations thereof.

7. The cleaner composition of claim 6, wherein said alkaline metal salt has a concentration in a range from about 1 g/l to about 16 g/l.

8. A method of cleaning a blood analyzer comprising the steps of:

(a) providing said formaldehyde-free cleaner composition of claim 1 to a blood analyzer;
(b) delivering said cleaner composition to parts of said blood analyzer, said parts being in contact with a sample mixture formed by a blood sample and one or more reagent during an analysis of said blood sample;
(c) contacting said parts with said cleaner composition for a period of time; and
(d) rinsing said cleaner composition out from said blood analyzer.

9. A formaldehyde-free cleaner composition comprising an aqueous solution of:
(a) one or more surfactant;
(b) at least two non-formaldehyde releasing antimicrobials comprising 5-chloro-2-methyl-4-isothiazolin-3-one, 2-methyl-4-isothiazolin-3-one, 1,2 benz-isothiazolin-3-one, or derivatives thereof, said non-formaldehyde releasing antimicrobials being in a concentration range from about 0.03 g/l to about 0.8 g/l;
(c) a proteolytic enzyme;
(d) one or more alkaline metal salt; and
(e) a buffer to maintain a pH of said cleaner composition in a range from about 7 to about 12;
said cleaner composition being absent of formaldehyde-releasing agent, substantially free of formaldehyde, and effective in inhibiting growths of bacteria, yeasts and fungi in a blood analyzer.

10. The cleaner composition of claim 9, wherein said cleaner composition has a formaldehyde concentration equal or less than 1 ppm.

11. The cleaner composition of claim 9, wherein said proteolytic enzyme is a subtilisin.

12. The cleaner composition of claim 9, wherein said surfactant is a nonionic surfactant, an anionic surfactant, or combinations thereof.

13. The cleaner composition of claim 9, wherein said alkaline metal salt is an alkaline metal halide, an alkaline metal formate, or combinations thereof.

14. The cleaner composition of claim 9, wherein said buffer is sodium carbonate, sodium bicarbonate, boric acid, glycylglycine, glycine, tris hydroxymethylaminoethane, N-tris(hydroxymethyl)methyl-2-aminoethane sulfonic acid, N-2-hydroxyehtylpiperazine-N'-2-ethanesulfonic acid, N-2-hydroxyethyl piperazine-N'-3-propane sulfonic acid, 2-(N-cyclohexylamino) ethane sulfonic acid, piperazine-1,4-bis (2-ethane sulfonic acid), or 3-((tris(hydroxymethyl) methyl)amino)propanesulfonic acid, or combinations thereof.

15. A method of cleaning a blood analyzer comprising the steps of:
(a) providing said formaldehyde-free cleaner composition of claim 9 to a blood analyzer;
(b) delivering said cleaner composition to parts of said blood analyzer, said parts being in contact with a sample mixture formed by a blood sample and one or more reagent during an analysis of said blood sample;
(c) contacting said parts with said cleaner composition for a period of time; and
(d) rinsing said cleaner composition out from said blood analyzer.

16. A formaldehyde-free cleaner composition comprising an aqueous solution of:
(a) one or more surfactant;
(b) a first isothiazolone compound;
(c) a second isothiazolone compound; and
(d) a third isothiazolone compound;
said isothiazolone compounds being in a concentration range from about 0.03 g/l to about 0.8 g/l, said cleaner composition being absent of formaldehyde-releasing agent and having a formaldehyde concentration equal or less than 1 ppm, and being effective in inhibiting growths of bacteria, yeasts and fungi in a blood analyzer.

17. The cleaner composition of claim 16, wherein said first isothiazolone compound is 5-chloro-2-methyl-4-isothiazolin-3-one, or derivatives thereof.

18. The cleaner composition of claim 16, wherein said second isothiazolone compound is 1,2 benzisothiazolin-3-one, or derivatives thereof.

19. The cleaner composition of claim 16, wherein said second isothiazolone compound is 2-methyl-4-isothiazolin-3-one, or derivatives thereof.

20. The cleaner composition of claim 16, wherein said surfactant is a combination of two non-ionic surfactants, or a combination of a non-ionic surfactant and an anionic surfactant.

21. The cleaner composition of claim 16 further comprising:
a proteolytic enzyme;
an alkaline metal formate;
an alkaline metal halide; and
a buffer to maintain a pH of said cleaner composition in a range from about 7 to about 12.

22. The cleaner composition of claim 21 wherein said proteolytic enzyme is a subtilisin.

23. The cleaner composition of claim 21 wherein said buffer is sodium carbonate, sodium bicarbonate, boric acid, glycylglycine, glycine, tris hydroxymethylaminoethane, N-tris(hydroxymethyl)methyl-2-aminoethane sulfonic acid, N-2-hydroxyehtylpiperazine-N'-2-ethanesulfonic acid, N-2-hydroxyethyl piperazine-N'-3-propane sulfonic acid, 2-(N-cyclohexylamino) ethane sulfonic acid, piperazine-1,4-bis (2-ethane sulfonic acid), or 3-((tris(hydroxymethyl) methyl) amino) propanesulfonic acid, or combinations thereof.

24. A method of cleaning a blood analyzer comprising the steps of:
(a) providing said formaldehyde-free cleaner composition of claim 21 to a blood analyzer;
(b) delivering said cleaner composition to parts of said blood analyzer, said parts being in contact with a sample mixture formed by a blood sample and one or more reagent during an analysis of said blood sample;
(c) contacting said parts with said cleaner composition for a period of time; and
(d) rinsing said cleaner composition out from said blood analyzer.

* * * * *